(12) United States Patent
Lawson et al.

(10) Patent No.: US 9,243,988 B2
(45) Date of Patent: Jan. 26, 2016

(54) SYSTEM AND METHOD FOR MONITORING BUBBLE FORMATION WITHIN A REACTOR

(75) Inventors: Kevin W. Lawson, Houston, TX (US); Lawrence C. Smith, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 349 days.

(21) Appl. No.: 13/702,861

(22) PCT Filed: Jul. 8, 2010

(86) PCT No.: PCT/US2010/041349
§ 371 (c)(1),
(2), (4) Date: Feb. 14, 2013

(87) PCT Pub. No.: WO2012/005729
PCT Pub. Date: Jan. 12, 2012

(65) Prior Publication Data
US 2013/0171735 A1  Jul. 4, 2013

(51) Int. Cl.
*G01N 35/08* (2006.01)
*G01N 9/36* (2006.01)
(Continued)

(52) U.S. Cl.
CPC . *G01N 9/36* (2013.01); *B01J 8/001* (2013.01); *B01J 8/06* (2013.01); *B01J 19/0033* (2013.01); *B01J 19/2435* (2013.01); *C08F 10/00* (2013.01); *B01J 2219/002* (2013.01); *B01J 2219/0011* (2013.01); *B01J 2219/0022* (2013.01); *B01J 2219/00065* (2013.01); *B01J 2219/00094* (2013.01); *B01J 2219/00216* (2013.01); *B01J 2219/00231* (2013.01); *B01J 2219/00238* (2013.01); *B01J 2219/00259* (2013.01); *B01J 2219/00272* (2013.01); *C08F 110/06* (2013.01); *C08F 210/06* (2013.01); *C08F 2400/02* (2013.01); *Y10T 436/12* (2015.01)

(58) Field of Classification Search
None
See application file for complete search history.

(56) References Cited

U.S. PATENT DOCUMENTS

| 3,636,326 A | 1/1972 | Smith et al. |
| 4,620,049 A | 10/1986 | Schmidt et al. |

(Continued)

FOREIGN PATENT DOCUMENTS

| EP | 0 432 555 | 6/1991 |
| EP | 0 900 590 | 3/1999 |

(Continued)

OTHER PUBLICATIONS

Chilekar et al., "Bubble Size Estimation in Slurry Bubble Columns From Pressure Fluctuations", AICHE Journal, vol. 51, No. 7, pp. 1924-1937, May 2, 2005.

*Primary Examiner* — Robert Xu
(74) *Attorney, Agent, or Firm* — Chad A. Guice (57) ABSTRACT

Bubble formation is monitored in a reactor such as a loop polymerization reactor which effectively operates at pressures above or near the vapor pressure of a circulating slurry liquid. The method measures a property of the reactor composition at a first location within the reactor, and then at a second location within the reactor. The process is repeated, followed by determining if the difference in measured property varies from a reference difference, derived under bubble-free conditions. When the difference in measured physical property has changed relative to the reference difference, an effect may be implemented, e.g., increase of reactor pressure, decrease of composition vapor pressure, and decrease of reactor temperature, to an extent sufficient to reduce or eliminate bubbling.

19 Claims, 2 Drawing Sheets

(51) Int. Cl.
*B01J 8/00* (2006.01)
*B01J 8/06* (2006.01)
*B01J 19/00* (2006.01)
*B01J 19/24* (2006.01)
*C08F 10/00* (2006.01)
C08F 110/06 (2006.01)
C08F 210/06 (2006.01)

(56) References Cited

U.S. PATENT DOCUMENTS

| | | | |
|---|---|---|---|
| 5,682,309 A | 10/1997 | Bartusiak et al. | |
| 6,204,344 B1 | 3/2001 | Kendrick et al. | |
| 6,301,546 B1 | 10/2001 | Weinstein et al. | |
| 6,718,234 B1 | 4/2004 | Demoro et al. | |
| 6,797,792 B2 * | 9/2004 | MacKenzie | 526/161 |
| 7,678,341 B2 | 3/2010 | Smith | |
| 2002/0065445 A1 | 5/2002 | Arrivat et al. | |
| 2005/0020784 A1 | 1/2005 | Noll | |
| 2007/0003450 A1 | 1/2007 | Burdett et al. | |
| 2008/0171838 A1 * | 7/2008 | Fouarge | 526/64 |
| 2010/0289482 A1 | 11/2010 | Markel et al. | |

FOREIGN PATENT DOCUMENTS

| | | |
|---|---|---|
| WO | WO 01/82008 | 11/2001 |
| WO | WO 2009/107927 | 9/2009 |
| WO | WO 2011/149769 | 12/2011 |

\* cited by examiner

SYSTEM AND METHOD FOR MONITORING BUBBLE FORMATION WITHIN A REACTOR

CROSS-REFERENCE TO RELATED APPLICATIONS

This is a National Stage Application filed under 35 U.S.C. 371 and claims priority to and the benefit of International Application No. PCT/US2010/041349 entitled "System And Method For Monitoring Bubble Formation Within A Reactor," which was filed on Jul. 8, 2010.

FIELD

This invention relates to systems and methods for monitoring bubble formation within a reactor, e.g., a loop polymerization reactor for producing polypropylene and/or polyethylene, by comparing physical properties at locations within a reactor.

BACKGROUND

Polypropylene and polyethylene homopolymers and copolymers are produced in a variety of reactors, such as loop polymerization reactors (e.g., slurry loop reactors).

Within the reactor, it is often desirable to increase the temperature within the reactor to improve catalyst efficiency, increase product crystallinity and/or increase the energy efficiency to flash liquid components from the solid product. It may also be desirable to increase the hydrogen concentration of the reactor composition (e.g., slurry) to reduce the molecular weight of the resultant product. However, these adjustments also increase the vapor pressure of the composition, which may cause gas bubbles to form if the vapor pressure is sufficiently close to, or exceeds, the operating pressure of the reactor. The bubbles can cause operational difficulties, such as errors in density measurements, diminished slurry circulation, or loss of slurry circulation resulting in reactor shutdown.

However, the vapor pressure of the slurry is difficult to estimate because conditions within the reactor (e.g., concentrations of components) are difficult to determine. Specifically, it is difficult to achieve mass balance of the hydrogen and "unknown" components of the liquid vapor pressure due to unmetered losses of hydrogen and other components and low accuracy of hydrogen reaction rate estimates. Moreover, the nature of the reaction slurry (solid reactive polymer particles dispersed in the reaction liquid) make it extremely difficult to reliably sample and measure component concentrations directly.

When a bubbling condition limit is reached or even approached, measures can be taken to restore or retain the slurry in its non-bubbling condition. One approach is to reduce the slurry temperature. Such reduction can be effected by reducing the temperature of, or increasing the flowrate of, a cooling liquid that surrounds the reactor, e.g., in an external cooling jacket surrounding a leg of the reactor loop. U.S. Pat. No. 7,678,341, incorporated herein by reference for this purpose, discloses a process for cooling polymerization reactors in the preparation of polyolefins.

WO/2001/082008 discloses a method for monitoring signals associated with downstream process equipment, e.g., electrical current, voltage or frequency signal, hydraulic pressure signals, or pneumatic pressure signals, to detect transients present in the signal that infer an associated change in product quality. An upstream process parameter can be adjusted in response to the inferred change in quality of the product, e.g., polypropylene.

U.S. Pat. No. 6,301,546 discloses detecting and monitoring changes in the properties of a fluidized bed of catalyst solids used to make synthesis gas which measures the magnitude of differential pressure fluctuations taken at different levels of bed elevation. Fluctuations in the pressure difference measured across a vertical section of the bed are related to the size of vapor-solid "bubbles" in the fluidized solids and can be used to track changes in the bed.

U.S. Pat. No. 6,718,234 discloses a system for online inference and control of physical and chemical properties of polypropylene and its copolymers. The system uses models for the inference of physical and chemical properties that are not continuously measured and relevant models to control these properties. Controlled variables include the power of the circulation pump, the opening of the valve that controls the temperature of each loop reactor, and the difference between the reactor temperature and the bubble point of the liquid within each loop reactor.

However, to date, there are no reliable analytical methods to detect bubbling within the reactor so that measures can be taken to limit or eliminate it. As such, to err on the side of caution, polymerization reactors typically must operate at pressures well above the vapor pressure of the slurry liquid circulating through the reactor.

That said, the desire to reduce catalyst cost and increase crystallinity and melt flow rates (MFRs) of the homopolymers and copolymers (e.g., impact copolymers) creates an incentive to operate the reactors at higher reactor temperatures and increased hydrogen concentrations. Moreover, the desire to increase plant capacity to reduce the capital and operating cost per unit of production creates an incentive to raise the reactor operating temperature. However, these adjustments tend to increase vapor pressure of the circulating slurry in the reactor.

That said, it would be useful to provide a method for determining when a slurry liquid circulating through a reactor has reached or surpassed a point at which bubble formation occurs to provide improved product and reactor efficiency while avoiding excessive bubbling or near-bubbling conditions.

SUMMARY

It has now been discovered that as the vapor pressure of the reaction slurry in a reactor nears operating pressure, differences in physical properties of the slurry arise at different locations within the reactor as a result of the hydrostatic head—the pressure at a given point in a liquid measured in terms of the vertical height of a column of the liquid needed to produce the same pressure. Slurry density and slurry temperature are especially sensitive to hydrostatic head effects when a reactor has reached or surpassed the bubble point. By measuring such physical properties at the top of the reactor and comparing them to properties at the bottom of the reactor, the onset of bubbling can be detected. Bubbling can then be controlled or avoided by altering conditions in the reactor, e.g., by lowering temperatures or hydrogen pressures, permitting operation of the reactor at or near optimal levels for a particularly desired product.

In one aspect, the present invention relates to a method for monitoring bubble formation within a reactor comprising:
 (a) measuring a property of a composition within the reactor at a first location to obtain a first measured value;

(b) measuring the property at a second location within the reactor to obtain a second measured value;
(c) determining a measured difference between the first measured value in (a) and the second measured value in (b); and
(d) comparing the measured difference with a reference difference to determine bubble formation.

In another aspect, the present invention relates to a loop polymerization reactor comprising a plurality of legs and a pump, the reactor comprising a composition containing a vaporizable liquid, the reactor further comprising:
(a) a first device for measuring a physical property of the composition to obtain a first value, wherein the first device is located at substantially the bottom of the leg that feeds the pump;
(b) a second device for measuring the physical property of the composition to obtain a second value, wherein the second device is located at substantially the top of the leg that feeds the pump;
(c) a third device for calculating the difference between the first value of (a) and the second value of (b); and
(d) a fourth device for comparing the difference of (c) with a reference difference wherein the reference difference reflects substantially bubble-free conditions.

DETAILED DESCRIPTION

In recent years, advances in catalysis and other process conditions have allowed for increased polymer production rates. Increased polymer production rates increase the heat of reaction, which can cause unwanted bubble formation within the liquid slurry. Accordingly, there is a need to monitor the liquid slurry to ensure that it does not reach bubbling conditions.

That said, the invention relates to a method for monitoring bubble formation within a reactor comprising: (a) measuring a property of a composition within the reactor at a first location to obtain a first measured value; (b) measuring the property at a second location within the reactor to obtain a second measured value; (c) determining a measured difference between the first measured value in (a) and the second measured value in (b); and (d) comparing the measured difference with a reference difference of the property.

Any type of reactor may be used herein. In one embodiment, the reactor is suitable to make polyolefins (e.g., polypropylene and polyethylene). In one embodiment, the reactor is a loop polymerization reactor. Loop polymerization reactors have a series of straight pipes connected by bent pipes, which form a continuous loop. Most loop reactors have two, four, six, or eight straight pipe segments, which are called legs. The legs may be substantially vertical. An example of such a loop-slurry reactor is described in U.S. Pat. No. 5,565,175, which is incorporated by reference for this purpose. Other examples of suitable loop reactors include those described in US Pub. Nos. 2009/0023872 and 2007/0022768, and are incorporated herein by reference for this purpose. Conveniently, the loop polymerization reactor is a bulk polypropylene reactor.

One aspect of the present invention is directed to a series polypropylene reactor comprising a first and an optional second loop reactor (or first or second "loop") allowing flow of the slurry (e.g., polypropylene, catalyst, hydrogen and propylene (and optionally a diluent)) therebetween, wherein each loop comprises from two to eight legs, each leg having fluid connections therebetween. The "flow" of materials can be assisted by pumps, pressure differentials and other means as is commonly known in the art, the flow of materials in certain embodiments achieved though fluid connections such as piping, conduits and other means of allowing liquids and/or suspensions (e.g., a slurry of liquid propylene and solid polymer material) as is commonly known in the art to flow from one place to another without exposure to the atmosphere. In one embodiment, comonomer may also be injected into the first, second, or both loops. Comonomers include ethylene and $C_4$ to $C_{12}$ alpha-olefins, or cyclic olefins. Preferable comonomers include ethylene, 1-butene, 1-pentene, 1-hexene, and 1-octene. It will be understood that other types of reactors, such as gas phase reactors, may be used in accordance with the present invention.

The reactor houses a composition (e.g., a slurry) comprising one or more components. Components include olefin monomer (e.g. propylene and/or ethylene), catalyst, hydrogen, polyolefin (e.g., polypropylene or polyethylene), contaminants, scavengers, additives and diluents which may be circulated therein. In one embodiment, the composition is an at least partially vaporizable liquid. Propane can also be present as a component, e.g., as propylene impurity or vapor pressure decreasing component. It will be understood that the components of the composition may be supplied to the reactor as reactants (e.g., olefin monomer, catalyst and hydrogen), or may be generated during polymerization (e.g., polyolefin). The composition may comprise, for example, at least monomer, solid catalyst particles, and solid polypropylene granules. In another embodiment, the composition comprises at least one of ethylene, propane, propylene, hydrogen, and polypropylene. As used herein, "polypropylene" includes both homopolymers of propylene and copolymers of propylene and another monomer-derived unit where the propylene-derived units comprise at least 50 wt % of the polymer. As used herein, "polyethylene" includes both homopolymers of ethylene and copolymers of ethylene and another monomer-derived unit where the ethylene-derived units comprise at least 50 wt % of the polymer.

The catalyst can be a suitable polymerization catalyst, such as a titanium/magnesium chloride based Ziegler-Natta catalyst or a metallocene catalyst, such as a metallocene catalyst comprising a Group 4 metal from the Periodic Table of Elements.

As discussed above, the processes described herein comprise measuring a property of a composition within the reactor at a first location to obtain a first measured value and measuring the property at a second location within the reactor to obtain a second measured value.

The property may be any property of the composition or reactor that can be used to indicate the formation of bubbles. In various embodiments, the property is a physical property. For example, the property may be temperature and/or density of the composition within the reactor.

Figure 1:
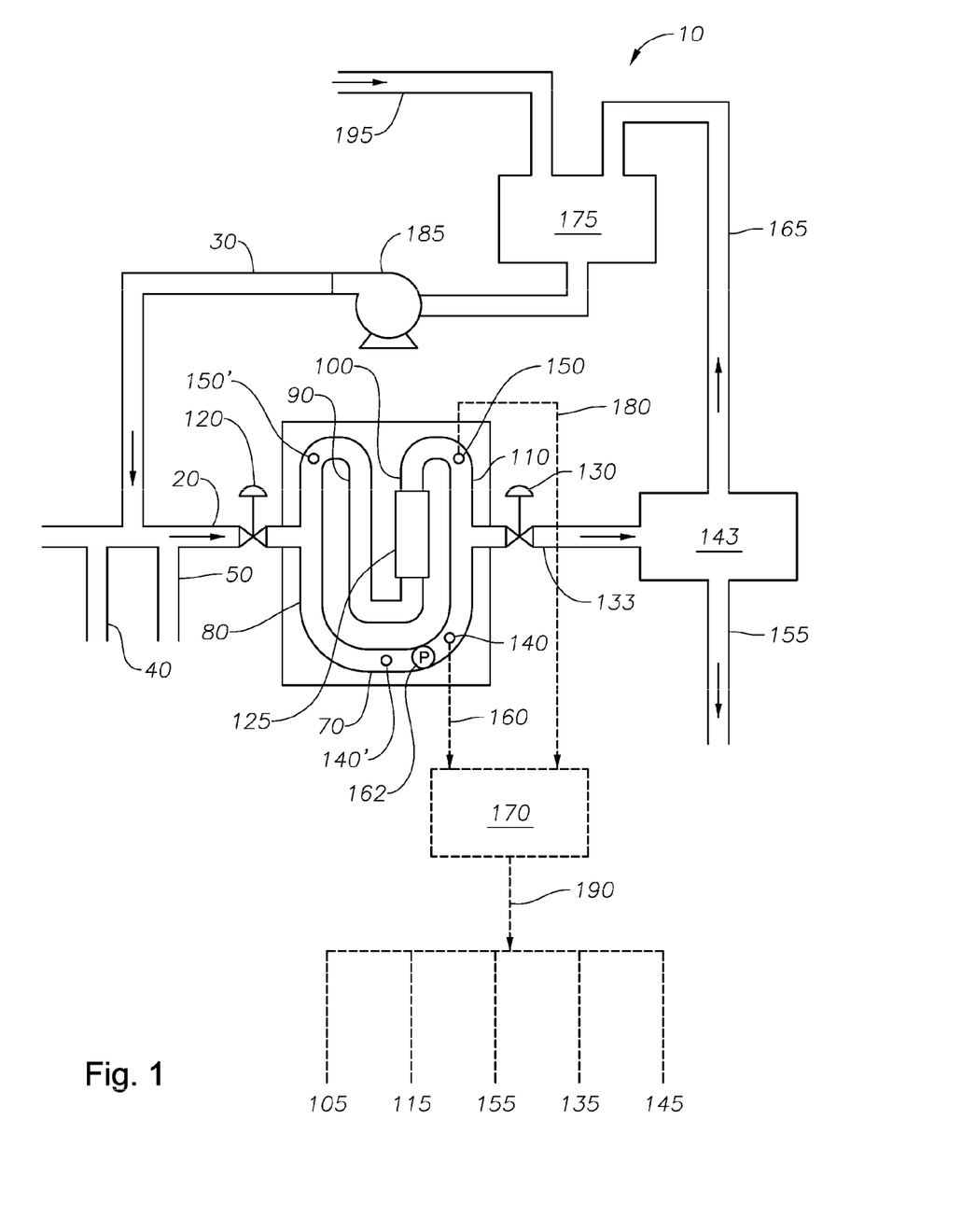
FIG. 1 is a process flow diagram of a polypropylene loop polymerization reactor illustrating a method of bubble control.

Referring now to FIG. 1, in an embodiment of the invention, the measured property taken, say, at the first sensor 140 and/or the second sensor 150, is temperature of the composition. Examples of suitable thermometers include in-line thermometers that are inserted into the path of the recirculating slurry mixture.

The property may be measured using any known or hereinafter devised system or method, e.g., sensors and the like. Examples of suitable temperature sensors include at least thermocouples and resistance temperature detector (RTD) which may be installed in a thermowell device or optionally directly into the process stream. Where the measured property is composition density, densitometers or density meters may be used as sensors. Examples of suitable densitometers include in-line density meters, ultrasonic density meters, and nuclear source density meters. Other measurements of the process include component analyzers to determine the composition of feed and recycle streams, flow meters, and weight scales.

In various embodiments, the second location is at a different operating pressure than the first location.

As illustrated in FIG. 1, first sensor 140 (i.e., the first location) is at the substantially the lowest point of the leg that feeds pump 162 and second sensor 150 (i.e., the second location) is at substantially the highest point of the leg that feeds pump 162.

In another embodiment, first sensor 140' (the first location) is at substantially the lowest point of the leg into which pump 162 discharges and the second sensor 150 (second location) is at substantially the highest point of the leg that feeds pump 162.

In another embodiment first sensor 140' (the first location) is at substantially the lowest point of the leg into which pump 162 discharges and sensor 150' (the second location) is at substantially the highest point of the leg into which pump 162 discharges.

In one embodiment, the first location is at substantially the highest pressure point in the reactor and/or the second location is at substantially the lowest pressure point in the reactor. For example, within a slurry loop reactor, the highest pressure point is typically the site within the reactor at which the circulating pump discharges. It is usually found at or near the lowest point within the reactor. Similarly, the lowest pressure point will be the site within the reactor at which the slurry enters the loop reactor leg connected to the circulating pump suction. It is usually found at or near the uppermost location within the reactor.

As discussed above, the processes described herein may further comprise: (c) determining a measured difference between the first measured value in (a) and the second measured value in (b). Typically, the measured difference will be determined by subtraction of the second measured value from the first measured value.

As discussed above, the processes described herein may further comprise: (d) comparing the measured difference between the first measured value in (a) and the second measured value in (b) with a reference difference of the property.

Conveniently, the reference difference is equal to the difference between the value of the physical property at the first location and the value of the physical property at the second location at substantially bubble-free conditions.

In various embodiments, the "substantially bubble-free conditions" used to determine the reference difference include a low hydrogen concentration or a low composition temperature. For present purposes, "low hydrogen concentration" means hydrogen concentration at levels sufficiently low to provide a liquid vapor pressure less than the desired operating pressure throughout the reactor at the desired reactor operating temperature. "Low composition temperature" means temperatures of reactor composition measured at one or more points within a reactor is sufficiently low to prevent bubbling within the circulating liquid slurry reactor composition and provides a liquid vapor pressure less than the desired operating pressure throughout the reactor at the desired liquid phase hydrogen concentration.

In one embodiment, the "substantially bubble-free conditions" used to determine the reference difference is obtained by thermodynamic calculations and evaluation of suspected cases of supposed bubble formation in the loop reactors. Suspected cases of bubble formation include periods of recirculation pump amp oscillations and densitometer measurement noise. These are two of the conditions that signal a risk of bubble formation when running close to the bubble point conditions. By reducing the amount of hydrogen or thinning the slurry concentration, further evidence of bubble formation is obtained by the nature and effect of the corrective action.

In various embodiments, the process may further comprise repeating steps (a) to (d), for example, on an intermittent or continuous basis.

Conveniently, the method further comprises implementing one or more effects when the difference in measured property diverges by a predetermined amount relative to the reference difference. As used herein, "a predetermined amount" can mean a deviation from the reference difference which nevertheless allows operation of the reactor within commercially acceptable limits, especially in terms of the production of commercially acceptable polymer product.

Effects include one or more of notifying a reactor operator, increasing the reactor pressure, decreasing the composition vapor pressure, or decreasing the reactor temperature to an extent sufficient to reduce or eliminate bubbling; maintaining the vapor pressure of the composition at a maximum value without bubble formation; and maintaining the vapor pressure of the composition at a maximum value with a limited amount of bubbling. By "maximum value" is meant the highest possible vapor pressure that can be maintained without onset of problems known to be associated with excessive bubble formation; e.g., recirculation pump amp oscillations and densitometer measurement noise.

Conveniently, an effect is implemented when the measured difference in said property measurements becomes significantly different from the reference difference.

The effect may be any action that lowers the vapor pressure of the composition or increases the reactor operating pressure. Effects include alert to the process operator, an automated process control sequence/interlock, or emergency shutdown of the reactor. In one embodiment of the invention, the effect comprises altering at least one process parameter. For present purposes, a "process parameter" means a variable that is known in the art to affect liquid vapor pressure or reactor operating pressure, including temperature, composition, especially hydrogen concentration, feed and discharge rates.

Conveniently, statistical methods are applied to determine whether the measured difference in the physical property measurements is significantly different from the reference difference. An effect is typically implemented when the measured difference in said physical property measurements becomes significantly different from the reference difference. What constitutes a significant difference can be determined, for example, by desired product characteristics, desired operational efficiency of the reactor, as well as operational experience.

In one embodiment, the effect is continuously implemented to maintain statistical control of the measured difference in said physical property measurements, and optionally, statistical control is maintained by at least one of open-loop or manual feedback control, closed-loop or automatic feedback control, and automatic feed forward control.

In yet another embodiment of the invention, the effect comprises activation of an event sequence that that reduces the reactor vapor pressure, preferably to a desired range within a fixed period. For example, the event sequence may reduce the reactor temperature by causing the temperature control system to implement full cooling of the reactor. The temperature control system can implement full or partial cooling of the reactor by any suitable means, e.g., by controlling heat exchangers surrounding the reactor piping, or reducing or eliminating the flow of added heat to the reactor.

In one embodiment, the event sequence slows or stops polymerization by providing a reaction inhibitor, e.g., carbon monoxide, directly or indirectly into the loop reactors. In various embodiments, the event sequence can slow polymerization by reducing or stopping the addition of catalyst to the reactor. By "full cooling" it is meant the reactor heat removal system is operated at its full capacity, which may include design or environmental limitations.

For present purposes, automatic feedback control relates to a control scenario wherein a sensing device senses and a processor automatically responds with an effect to changes in a parameter that it controls, e.g., automatically adjusting the reaction slurry temperature controller setpoint to maintain a statistically constant value of (c). Manual feedback control relates to a control scenario wherein a human operator responds to a signal or message provided by a sensing device and/or processor, e.g. manually reducing the reaction slurry temperature controller setpoint. Automatic feed forward control relates to a control scenario wherein the future state of a sensing device is predicted from the current state of other sensing devices in the process and an automatic response is affected, e.g. a sudden increase in hydrogen concentration in a first slurry loop reactor is predicted to lead to a corresponding increase in the hydrogen concentration in a second slurry loop reactor connected downstream in series with the first slurry loop reactor, thus an automatic response to reduce the second reactor feed hydrogen or to reduce the second reactor temperature can be affected by a processor to prevent excessive bubble formation.

The processor may be used to calculate the difference in signals and compares this measured difference to a similarly obtained reference difference obtained under known bubble-free conditions; and implements an effect to maintain the reactor at a non-bubbling condition, or alternately, at the bubble point where bubbling is initiated or below an undesirable level of bubble formation. The bubble point or undesirable level of bubble formation can be independently detected by evaluating pump operation (e.g. vibration, audible pump noise, variation in power draw, etc.).

In still yet another aspect of the invention, the vapor pressure of the composition is controlled by varying at least one of the temperatures of the reactor, and varying the amount of a vapor pressure increasing component in the composition, and varying the amount of a vapor pressure decreasing component in the composition.

Optionally, the vapor pressure increasing component is selected from hydrogen and ethylene, and the vapor pressure decreasing component is propane.

Optionally, the extent of bubbling is relatable to at least one of variation in power draw of a reactor pump used to circulate reactor composition, pump cavitation, variation in reactor temperature and/or density control, and variation in reactor reactant addition rates.

Referring to the exemplary embodiment illustrated in FIG. 1 of a method for monitoring or avoiding bubble formation in system 10, namely, a slurry loop polymerization reactor for polymerizing olefins which operates with a circulating liquid slurry composition. Propylene feed enters a reactor inlet line 20 via propylene feed line 30, along with polymerization catalyst via catalyst inlet line 40, and optional hydrogen via hydrogen inlet line 50. The resulting liquid slurry composition mixture enters slurry loop reactor 70 having a plurality of legs, 80, 90, 100, and 110. Each leg is fluidly connected to another leg at each end by bent piping. In the embodiment depicted in FIG. 1, the reactor's single loop includes four legs. In another embodiment (not shown), the series reactor system comprises a first loop and a second loop wherein each loop comprises from four to eight legs. While not shown in FIG. 1, it should be apparent to those skilled in the art that there will be a fluid connection between the loops to allow flow of liquid and/or slurry and/or gaseous material therebetween.

Propylene and, if added, hydrogen and other monomers and propane, can be separated from the polymer being produced and recycled back to the first, second, or more loops, wherein one or more of each leg of the loop or loops can be jacketed for cooling with a heat transfer medium, e.g., water. In a two-loop embodiment of the series reactor (not shown), recycled propylene and hydrogen may be routed into the second loop through a recycle conduit. Heat of reaction can be removed by use of liquid flow, preferably water, through the jacket(s) 125. In one embodiment, each jacket is independently supplied water, and in another embodiment, water flows through two or more jackets in series. The circulating slurry or liquid in each loop is kept preferably at a temperature of from 50° C. to 90° C., more preferably between 60° C. and 75° C., even more preferably between 68° C. and 75° C.

Entry and exit from slurry loop reactor 70 can be controlled by inlet valve 120 and outlet valve 130, respectively. A first sensor 140 is located at a first location of slurry loop reactor 70 (e.g., on a lower portion of a leg of reactor 70) to measure a physical property and a second sensor 150 is located at a second location of slurry loop reactor 70 (e.g., on the upper portion of a leg of reactor 70) to measure the same physical property. First sensor 140 produces an electrical signal that is a function of the physical property measured, which signal is directed via line 160 to processor 170. Similarly, second sensor 150 produces an electrical signal that is a function of the physical property measured, which signal is directed via line 180 to processor 170. The processor calculates the difference in signals and compares this measured difference to a reference difference. When this difference in measured signals approaches or exceeds the fixed reference difference (i.e., reference difference obtained at or just before the bubble point), the processor triggers an output signal via line 190 that can implement an effect in response to bubbling or its imminent initiation, which response can control, prevent, eliminate, or at least reduce the bubbling.

Such an effect can include notification of a reactor operator 105, who can then manually initiate one or more procedures to prevent, eliminate, or reduce bubbling liquid in the reactor. The processor itself can directly initiate one or more effects to this end. Such effects can include one or more of: increasing of reactor pressure or decrease of reactor temperature and/or decreasing the composition vapor pressure 115, or maintaining the vapor pressure of the composition at a maximum value without bubble formation 155. Additionally or alternately, the effect can maintain the vapor pressure of the composition at a maximum value with a limit on extent of bubbling 135—extent of bubbling being relatable to at least one of variation in power draw of a reactor pump used to circulate reactor composition, pump cavitation (which can be indicated by increased pump power draw variation, vibration or audible noise), variation in reactor temperature control, and variation in reactor reactant addition rates.

These effects can be accomplished, e.g., by reducing partial pressure of a reactor composition component, say, hydrogen, by reducing the flow of hydrogen at inlet line 50. Another effect 145 can relate to decrease of reactor temperature, e.g., by controlling temperature of a heat exchange medium (or coolant, e.g., water) in a jacket 125 surrounding some or all of the reactor loop. Thus, vapor pressure of the composition can be controlled by varying at least one of: the temperature of the reactor, the amount of a vapor pressure increasing component in the composition, and the amount of a vapor pressure decreasing component in the composition. Vapor pressure increasing component can be selected from hydrogen, which can be added via line 50 and ethylene, which can be added to line 20 via any other suitable inlet. Vapor pressure decreasing components, such as propane, can be adjusted by controlling the propane concentration in propane liquid storage drum 175.

Controller 170 can slow or stop polymerization by triggering a valve that releases a reaction inhibitor, e.g., carbon monoxide, directly or indirectly into the loop reactors, e.g., via line 50. Alternatively, an event sequence can slow polymerization by controlling a valve that reduces or stops the addition of catalyst via line 40 to the reactor.

In an embodiment of the invention, the measured physical property taken, say, at the first sensor 140 and the second sensor 150, is composition temperature.

When polymerization has proceeded to a desired extent, e.g., as measured by the production rate the circulating slurry, whose circulation through the loop can be provided by a pressure differential, such as that provided by a suitable pump (not shown), e.g., axial flow elbow pump, can be withdrawn from the loop via line 133 wherein flow is controlled by reactor outlet valve 130. The pump inlet and outlet can be located at a suitable location in the loop, e.g., at the bottom of a leg comprising a loop. The slurry mixture passes through line 133 into separator 143, e.g., a propylene/polypropylene separator, wherein polymer is separated out and directed out of the separator as a polymer stream via line 155. Conduit 165 allows for the unreacted fluids and gases to be directed to the propane drum 175, whence they can be directed back to the reactor via lines 30 and 20, impelled by circulating pump 185. Fresh propylene can be added to the system via the propylene drum 175 through line 195. Propane concentration in the drum 175 can be controlled by taking an appropriate purge of propane enriched stream 165.

In any embodiments described herein, there may also be included in the fluid stream a diluent such as propane, or other hydrocarbon. The pressure of the reacting monomers and optional diluent in the loops can typically range from 2760 to 3930 kPa (400 psig to 800 psig), preferably between 3310 to 3930 kPa (480 and 570 psig).

Figure 2:
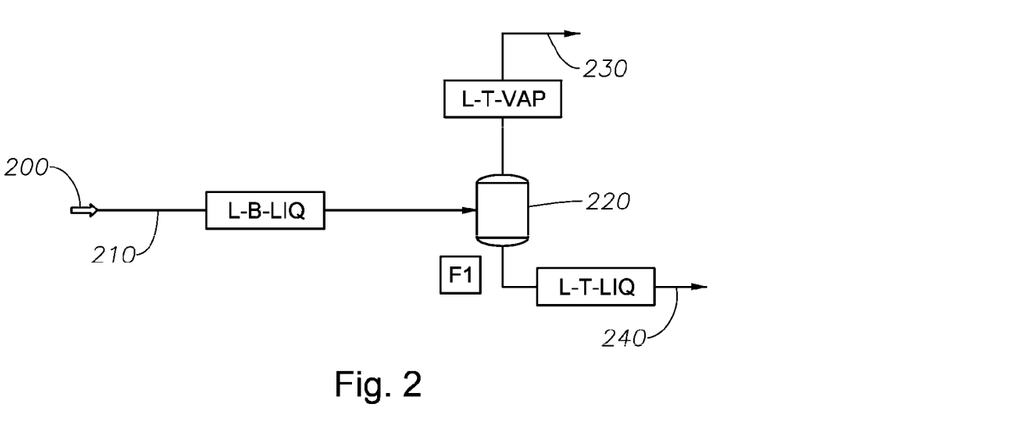
FIG. 2 is a process flow diagram showing a simulation of bubble formation in loop reactors using a flash drum.

FIG. 2 depicts a process flow diagram showing a simulation of bubble formation in a loop reactor using a flash drum to create a pressure differential similar to the pressure differential provided by the static head in a slurry loop reactor. A typical loop propylene feed is saturated with hydrogen (11,000 mol parts-per-million (ppm)) at 75° C. at 3930 kPa (167° F. at 570 psia) to form loop bottom bubble point liquid (L-B-LIQ) 200, which simulates a loop bottom liquid (corresponding to the slurry liquid as it is measured at a lower location in the reactor).

Liquid 200 is passed via line 210 to flash drum 220 operating at 3715 kPa (540 psia), which provides overhead stream 230 corresponding to a loop top vapor (L-T-VAP), and a bottoms stream 240 corresponding to the loop top slurry liquid (L-T-LIQ) as they are measured at an upper location in the reactor.

The flash is carried out at a pressure that simulates slurry moving up a reactor leg. Specifically, a flash differential pressure was determined to provide a similar effect as the hydrostatic head expected for a 135 foot (41 m) loop reactor by assuming a slurry density of 520 kg/m3 (32.4 lb/ft3). The resulting difference for such a reactor is calculated as about 215 kPa (31 psia), providing a flash pressure of 3715 kPa (540 psia).

Temperature at the top of the loop is expected to have significant effect on the results of this simulation. However, as a basis for estimating the range of the actual flash response, two realistic extremes are evaluated: an isothermal flash at 75° C. (167° F.) from 3930 kPa (570 psia) and a pseudo-adiabatic flash wherein it is assumed that reaction rate and heat removal rate through the reactor walls are not affected by change in temperature. Isothermal operation results are set out below in TABLE 1 and indicate that about 12 wt % of the liquid is flashed with the resulting vapor having a significantly lower density (but no temperature change). Pseudo-adiabatic operating results are set out below in TABLE 2 and indicate that about 4 wt % of the liquid is flashed with the resulting vapor having a significantly lower density and about 1° C. (2° F.) lower slurry temperature.

TABLE 1

| | Stream Name | | |
|---|---|---|---|
| | Loop Bottom Liquid (L-B-LIQ) | Loop Top Liquid (L-T-LIQ) | Loop Top Vapor (L-T-VAP) |
| Phase | Liquid | Liquid | Vapor |
| Temperature (° C.) | 75 | 75 | 75 |
| Pressure (bara) | 39 | 37 | 37 |
| Vapor Act. Density (kg/m$^3$) | n/a | n/a | 5.5 |
| Liquid Act. Density (kg/m$^3$) | 386 | 388 | n/a |
| Total Mass Rate (wt %) | 100 | 87 | 13 |

TABLE 2

| | Stream Name | | |
|---|---|---|---|
| | Loop Bottom Liquid (L-B-LIQ) | Loop Top Liquid (L-T-LIQ) | Loop Top Vapor (L-T-VAP) |
| Phase | Liquid | Liquid | Vapor |
| Temperature (° C.) | 75 | 73 | 73 |
| Pressure (bara) | 39 | 37 | 37 |
| Vapor Act. Density (kg/m$^3$) | n/a | n/a | 82 |
| Liquid Act. Density (kg/m$^3$) | 386 | 394 | n/a |
| Total Mass Rate (wt %) | 100 | 96 | 4 |

Analysis of the resulting data suggests several opportunities to measure bubble formation in a liquid slurry, provided the physical properties of the reaction slurry can be measured at different locations, e.g., the top and bottom, in the slurry loop reactor. With a standard densitometer mounted at the top and bottom, a significant change in slurry density can be measured.

Figure 3:
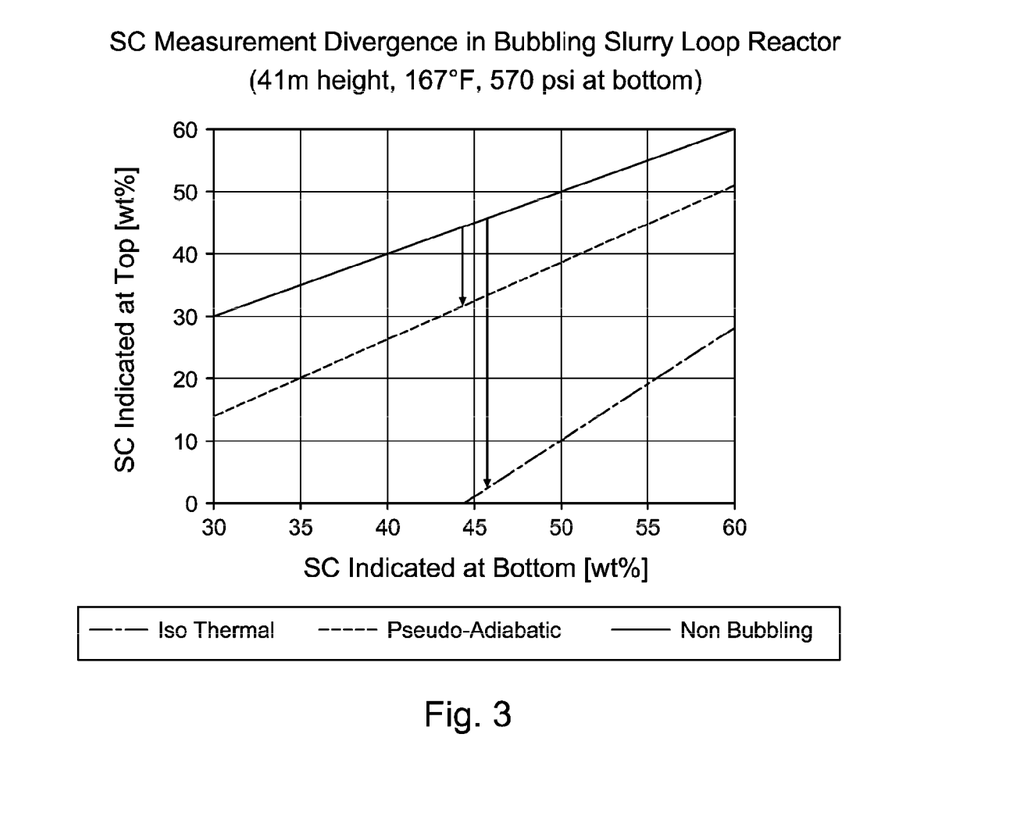
FIG. 3 is a graph illustrating calculated solids concentration at the top of a reactor vs. calculated solids concentration at the bottom of a reactor at its bottom bubble point (the point at which the reactor slurry begins to bubble at the bottom of the reactor) over a range of densities. Values for both isothermal and adiabatic operation are provided.

The standard correlation of the loop reactor slurry concentration to the nuclear instrument source strength measured at the detector from the two densitometers would begin to diverge as the slurry begins to bubble as shown by FIG. 3. With isothermal flashing, the calculations indicate the measurement at the top of the reactor would indicate only 1 wt % solids concentration (SC) for an actual 45 wt % solids concentration slurry at its bubble point at the bottom of the reactor. Even with pseudo-adiabatic flashing, the calculations indicate the measurement at the top of the reactor would indicate only 32 wt % solids concentration for an actual 45 wt % solids concentration slurry at its bubble point at the bottom of the reactor. Such differences are significant enough that two densitometers can be used to directly detect the onset of bubble formation.

For detecting bubble formation by temperature measurements within the reactor, one would have to assume that a "non-bubbling" difference in temperature provided by subtracting a temperature measured from the bottom of the reactor from a temperature measured at the top of the reactor would change by up to 2.5° C. (4° F.) as the bottom of the reactor approached saturation (and the onset of bubbling). With 50 wt % solids liquid slurry this temperature change would be less because of the energy that it takes to cool the solids say, about 1° C. (2° F.), depending on the heat capacity of PP solids vs. the liquid heat capacity. However, this temperature difference is within the confidence range of commercially available temperature sensors utilized in a reactor. Although the temperature sensor application of the invention would likely be less costly and easier to implement than the aforementioned density sensor, the temperature based method is not nearly as sensitive to bubbling as is the density based method.

The present invention can be further described as follows:
1. A method for monitoring bubble formation within a reactor comprising:
    a) measuring a property of the composition at a first location within the reactor to obtain a first measured value;
    b) measuring the property at a second location within the reactor to obtain a second measured value;
    c) determining a difference between the first measured value in (a) and the second measured value in (b); and
    d) comparing the difference in (c) with a reference difference for the property to monitor bubble formation.
2. The method of 1, wherein the reference difference is determined under substantially bubble-free conditions.
3. The method of 1, further comprising:
    (e) continuously repeating steps (a) through (d).
4. The method of 1, further comprising implementing an effect when the difference diverges from the reference difference by a predetermined amount.
5. The method of 4, wherein the effect is at least one of: (i) notification of a reactor operator; (ii) increase of reactor pressure; (iii) decrease of composition vapor pressure; and (iv) decrease of reactor temperature.
6. The method of 5, wherein the effect is activation of an event sequence that reduces the vapor pressure of the composition in the reactor.
7. The method of 6, wherein the activation is one of manual or automatic.
8. The method of 6, wherein the reactor comprises a temperature control system, and the event sequence reduces the reactor temperature by causing the temperature control system to implement full cooling of the reactor.
9. The method of 6, wherein the event sequence at least one of stops or slows polymerization by providing a reaction inhibitor directly or indirectly into the reactor.
10. The method of 9, wherein the reaction inhibitor includes carbon monoxide.
11. The method of 6, wherein the event sequence slows polymerization by reducing or stopping the addition of a catalyst to the reactor.
12. The method of 4, wherein the effect is to control the vapor pressure of the composition at a maximum value with no bubble formation.
13. The method of 4, wherein the effect is to control the vapor pressure of the composition at a maximum value with a limit on amount of bubbling.
14. The method of 13, wherein the amount of bubbling is relatable to at least one of: (i) variation in power draw of the pump; (ii) cavitation of the pump; (iii) change of reactor temperature; (iv) variation in reactor density control; and (v) change of reactant addition rates.
15. The method of 13, wherein the vapor pressure of the composition is controlled by varying the temperature of the reactor.
16. The method of 13, wherein the vapor pressure of the composition is controlled by varying an amount of a vapor pressure increasing component in the composition.
17. The method of 16, wherein the vapor pressure increasing component is one or more of hydrogen and ethylene.
18. The method of 13, wherein the vapor pressure of the composition is controlled by varying an amount of a vapor pressure decreasing component in the composition.
19. The method of 18, wherein the vapor pressure decreasing component is propane.
20. The method of 1, wherein the physical property is one of composition temperature and composition density.
21. The method of 1, wherein the reactor is a loop polymerization reactor.
22. The method of 21, wherein the loop polymerization reactor is a bulk polypropylene reactor.
23. The method of 1, wherein the composition is a slurry comprising at least monomer, solid catalyst particles, and solid polypropylene granules.
24. The method of 1, wherein the composition comprises at least one of ethylene, propane, propylene, hydrogen, and polypropylene.
25. The method of 1, wherein the reactor is a substantially vertical loop reactor comprising a plurality of legs and the reactor comprising a circulating pump.
26. The method of 1, wherein the first location is substantially at the point of the highest operating pressure in the reactor and the second location is substantially at the point of the lowest operating pressure in the reactor
27. The method of 25, wherein the first location is at substantially the bottom of the leg that feeds the pump and the second location is at substantially the top of the leg that feeds the pump.
28. The method of 25, wherein the first location is at substantially the bottom of the leg into which the pump discharges and the second location is at substantially the top of the leg into which the pump discharges.
29. The method of 1, wherein the reference difference is determined at a low hydrogen concentration or a low composition temperature.
30. The method of 1, wherein statistical methods are applied to determine whether the difference is significantly different from the reference difference.

31. The method of 1, wherein an effect is implemented when the difference becomes significantly different from the reference difference.
32. The method of 1, wherein an effect is continuously implemented to maintain statistical control of the difference, and wherein statistical control is maintained by at least one of open loop feedback control, manual feedback control, automatic feedback control, and automatic feed forward control.
33. A loop polymerization reactor comprising a plurality of legs and a pump, the reactor comprising a composition containing a vaporizable liquid, the reactor further comprising:
   (a) a first device for measuring a physical property of the composition to obtain a first value, wherein the first device is located at substantially the bottom of the leg that feeds the pump;
   (b) a second device for measuring the physical property of the composition to obtain a second value, wherein the second device is located at substantially the top of the leg that feeds the pump;
   (c) a third device for calculating the difference between the first value of (a) and the second value of (b); and
   (d) a fourth device for comparing the difference of (c) with a reference difference wherein the reference difference reflects substantially bubble-free conditions.

All priority documents, patents, publications, and patent applications, test procedures (such as ASTM methods), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention claimed is:

1. A method for monitoring bubble formation within a reactor comprising:
   a) measuring a property of a composition within the reactor at a first location to obtain a first measured value, wherein the composition is a slurry comprising at least monomer, catalyst particles, and polyolefin;
   b) measuring the property at a second location to obtain a second measured value;
   c) determining a measured difference between the first measured value in (a) and the second measured value in (b); and
   d) comparing the measured difference in (c) with a reference difference to monitor bubble formation.
2. The method of claim 1, wherein the reference difference is equal to the difference between the value of the property at the first location and the value of the property at the second location determined under substantially bubble-free conditions.
3. The method of claim 1, further comprising: e) repeating steps (a) through (d).
4. The method of claim 1, further comprising implementing an effect when the measured difference in (c) diverges from the reference difference by a predetermined amount.
5. The method of claim 4, wherein the effect is at least one of: (i) notifying a reactor operator; (ii) increasing the operating pressure of the reactor; (iii) decreasing the vapor pressure of the composition; and (iv) decreasing the temperature of the reactor.
6. The method of claim 5, wherein the effect is activation of an event sequence that reduces the vapor pressure of the composition.
7. The method of claim 6, wherein the reactor comprises a temperature control system, and the event sequence reduces the temperature of the reactor by causing the temperature control system to implement full cooling of the reactor.
8. The method of claim 6, wherein the event sequence at least one of stops or slows polymerization by providing a reaction inhibitor directly or indirectly into the reactor.
9. The method of claim 8, wherein the reaction inhibitor includes carbon monoxide.
10. The method of claim 6, wherein the event sequence slows polymerization by reducing or stopping the addition of a catalyst to the reactor.
11. The method of claim 4, wherein the effect is to control the vapor pressure of the composition at a maximum value with no bubble formation or at a maximum value with a limit on amount of bubbling.
12. The method of claim 11, wherein the reactor comprises a pump to circulate the composition and the amount of bubbling is relatable to at least one of: (i) variation in power draw of the pump; (ii) cavitation of the pump; (iii) change of reactor temperature; (iv) variation in reactor density control; and (v) change of reactant addition rates.
13. The method of claim 11, wherein the vapor pressure of the composition is controlled by varying the temperature of the reactor.
14. The method of claim 11, wherein the vapor pressure of the composition is controlled by varying an amount of a vapor pressure increasing component in the composition.
15. The method of claim 11, wherein the vapor pressure of the composition is controlled by varying an amount of a vapor pressure decreasing component in the composition.
16. The method of claim 1, wherein the reactor is a loop polymerization reactor.
17. The method of claim 1, wherein the reference difference is determined at a low hydrogen concentration in the composition or a low composition temperature.
18. The method of claim 1, wherein an effect is implemented when the measured difference becomes significantly different from the reference difference, wherein statistical methods are applied to determine whether the measured difference in (c) is significantly different from the reference difference.
19. The method of claim 18, wherein an effect is continuously implemented to maintain statistical control of the measured difference, and wherein statistical control is maintained by at least one of open loop feedback control, manual feedback control, automatic feedback control, and automatic feed forward control.

* * * * *